United States Patent
Honma et al.

(10) Patent No.: US 6,545,166 B2
(45) Date of Patent: Apr. 8, 2003

(54) PROCESS FOR PRODUCING SPIRO ACETAL DERIVATIVE

(75) Inventors: Masao Honma, Kawasaki (JP); Atsushi Mashita, Kawasaki (JP); Hiroyasu Koto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/179,951

(22) Filed: Jun. 26, 2002

(65) Prior Publication Data

US 2003/0028037 A1 Feb. 6, 2003

(30) Foreign Application Priority Data

Jul. 13, 2001 (JP) ........................................ 2001-213025

(51) Int. Cl.[7] ............................................. C07D 319/06
(52) U.S. Cl. ....................................................... 549/335
(58) Field of Search ........................................... 549/335

(56) References Cited

PUBLICATIONS

Mateo et al, "Bifunctional Derivatives, etc" CA67: 100140 (1967).*

* cited by examiner

*Primary Examiner*—Patricia L. Morris
(74) *Attorney, Agent, or Firm*—Oblon, Spivak, McClelland, Maier & Neustadt, P.C.

(57) ABSTRACT

In this application is disclosed a process for producing 3,9-bis(2-chloroethyl)-2,4,8,10-tetraoxaspiro[5.5]undecane comprising a step of reacting acrolein, pentaerythritol, and hydrogen chloride at one step, according to which the compound can be obtained conveniently in high yields.

2 Claims, No Drawings

PROCESS FOR PRODUCING SPIRO ACETAL DERIVATIVE

BACKGROUND OF THE INVENTION

1. Technical Field of the Invention

The present invention relates to a process for producing 3,9-bis(2-chloroethyl)-2,4,8,10-tetraoxaspiro[5.5]undecane (hereinafter, sometimes abbreviated as Compound (I)) useful as a synthetic intermediate.

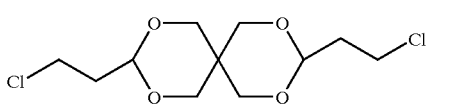

2. Related Art

Compound (I) is a useful intermediate raw material for synthesizing various bifunctional derivatives having a spiro acetal skeleton. As a known production method thereof, there is known a method comprising two steps, i.e., firstly, (1) the synthesis of 3,9-divinyl-2,4,8,10-tetraoxaspiro[5.5] undecane (hereinafter, abbreviated as Compound (II)) by reacting acrolein with pentaerythritol in the presence of p-toluenesulfonic acid, and successively, (2) the synthesis of Compound (I) by reacting Compound (II) with hydrogen chloride (Spanish Patent No. 324610 (1966)). According to Examples thereof, the yields in the reactions (1) and (2) are relatively high, i.e., 81.5% and 81%, respectively, but the method requires many operations owing to the fact that the method involves a two-step reaction, so that it is not necessarily efficient.

On the other hand, the synthesis of 1,1-dialkoxy-3-chloropropane by reacting acrolein, an alcohol such as methanol ethanol or the like, and hydrogen chloride has been hitherto known (Org. Syn. Coll. vol. 2, 137 (1943)). According to the literature, 1,1-diethoxy-3-chloropropane (hereinafter, abbreviated as Compound (III)) is synthesized by adding acrolein into ethanol saturated with dry hydrogen chloride gas, whereby the acrolein, the hydrogen chloride and the ethanol are reacted with each other. However, the yield is only 34% because various by-products are formed.

As an attempt to improve the yield by suppressing the formation of the by-products in the above reaction, there is a report that Compound (III) was obtained in 87.7 to 91% yields by adding an anhydrous ether solution of acrolein into anhydrous ether in which dry hydrogen chloride had been absorbed, followed by adding absolute ethanol and molecular sieves thereto (Proc. Jpn. Acad., Ser. B, 56(9), 573 (1980)). One of the points of this method lies in the exhaustive exclusion of water from the reaction system. Therefore, the method is not economical in the industrial use, because the raw materials should be made anhydrous and molecular sieves are used in a large amount.

SUMMARY OF THE INVENTION

Problem to be Solved by the Invention

In consideration of the above situation, it is an object of the present invention to provide a process for obtaining Compound (I) conveniently in high yields.

Means for Solving the Problem

As a result of the extensive studies for achieving the above object, the present inventors have found that Compound (I) can be obtained conveniently in high yields by reacting acrolein, pentaerythritol, and hydrogen chloride at one step. Based on such findings, they have accomplished the present invention.

Accordingly, the present invention relates to a process for producing 3,9-bis(2-chloroethyl)-2,4,8,10-tetraoxaspiro [5.5]undecane comprising a step of reacting acrolein, pentaerythritol, and hydrogen chloride at one step.

DETAILED DESCRIPTION OF THE INVENTION

In the following will be described the present invention in detail.

According to the present invention, acrolein is used in an amount of 1.6 to 3.0 moles, more preferably 2.0 to 2.5 moles, per 1 mole of pentaerythritol. The use of an excess of acrolein is not preferable because unreacted acrolein and 3-chloropropanal may remain in the reaction system.

In the reaction of the present invention, hydrogen chloride acts as the reaction catalyst as well as a reactant. Equimolar or more amounts of hydrogen chloride are required per 1 mole of acrolein to be used. Hydrogen chloride is used in the reaction after the dry gas thereof has been absorbed in a solvent. Alternatively, in the reaction of the present invention, hydrochloric acid can be also used instead of hydrogen chloride gas, in other words, the hydrogen chloride can be in the form of hydrochloric acid. In the aspects of the handleability and the economical efficiency, the use of hydrochloric acid is industrially more advantageous.

Since the aimed-at Compound (I) is a solid substance at ordinary temperature and is sparingly soluble in water, it is preferable to add to the reaction system, an inert solvent in which Compound (I) is soluble not only in the case of using hydrogen chloride gas but also in the case of using hydrochloric acid. The solvents usable include aromatic solvents such as toluene, xylene, tetramethylbenzene, and the like; aliphatic and alicyclic hydrocarbon solvents such as pentane, hexane, heptane, octane, nonane, petroleum ether, cyclopentane, cyclohexane, and the like; ethers such as diethyl ether, THF, and the like; acetonitrile; and the like. For the purpose of facilitating the post-treatment after the reaction, a solvent having a low solubility in water is suitable.

As other additives, in order to prevent the polymerization of acrolein, a polymerization inhibitor such as a multivalent phenol, e.g., hydroquinone, p-t-butylcatechol, or the like may be added in a slight amount.

The following will explain the reaction itself and subsequent post-treatment step after the reaction.

To pentaerythritol is added hydrochloric acid (and a solvent) or a solvent in which dry hydrogen gas has been absorbed. With stirring the resultant mixture, acrolein is added gradually thereto. Acrolein may be added after it has been mixed with a solvent and/or a polymerization inhibitor beforehand. Alternatively, the polymerization inhibitor may be added to 1a mixture of pentaerythritol and hydrogen chloride. The reaction proceeds as acrolein is added. The reaction mixture is kept at a temperature of −20° C. to 60° C., preferably 0 to 40° C.

After the completion of the reaction, hydrogen chloride present in excess is neutralized with an alkali (aqueous solution) of sodium hydrogen carbonate, sodium carbonate, sodium hydroxide, or the like. In that case, an organic layer containing the aimed-at Compound (I) can be easily separated, by using a solvent having a low solubility in water.

Since Compound (I) is used as an intermediate for synthesis, the purification is carried out according to the purity required in the subsequent synthetic reaction in which the compound is used as a raw material. In the simplest case, the above solution after the neutralization is provided as it is to the next reaction. On the other hand, in the case where a high purity is required, after the removal of the solvent by evaporation, the compound is isolated/purified, for example, by further distillation under reduced pressure or by recrystallization from an acetone-water mixed solvent, a methanol-water mixed solvent, or the like.

In the synthesis of 1,1-dialkoxy-3-chloropropane by reacting acrolein, an alcohol, and hydrogen chloride, it is common to use dry hydrogen chloride gas, because the reaction for acetalization is an equilibrium reaction involving the formation of water. In the process of the present invention, the aimed-at compound can be obtained in high yields even when hydrochloric acid is used. The reason may be presumed from the dissolving properties of the raw materials and the aimed-at Compound (I) as follows. That is, pentaerythritol is a crystalline substance having a high melting point (260° C.) and has characteristics that it is soluble in water, ethanol, glycerol, or the like but is insoluble in most of organic solvents. On the other hand, the aimed-at Compound (I) has a low solubility in water. Therefore, the reaction occurs or proceeds in hydrochloric acid, but the equilibrium is shifted by the precipitation of the aimed-at Compound (I) formed from the hydrochloric acid, so that it is considered that the aimed-at compound can be obtained in high yields.

EXAMPLES

In the following will be illustrated the example of the present invention, but the present invention is not restricted to the scope of the example.

Example 1

Into a 200-ml three-necked flask equipped with a dropping funnel, a stirrer, and a thermometer were charged 13.6 g (0.10 mol) of pentaerythritol, 20 mg of hydroquinone, 40 ml (about 0.42 mol) of about 33% hydrochloric acid, and 30 ml of toluene, and the mixture was stirred at room temperature, whereby the pentaerythiritol was dispersed. To the resulting mixture while stirred on a constant-temperature water bath with the mass temperature being kept at 15 to 20° C., 12.3 g (0.22 mol) of acrolein purified by distillation was added dropwise over a period of 0.5 hour. After the completion of the dropwise addition, the stirring of the reaction mixture was continued for another 2 hours while the reaction mixture was kept at the same temperature.

After the predetermined period of time, the reaction mixture was left to stand, whereby it was separated into an organic layer and an aqueous layer. The aqueous layer was washed twice with 30 ml of toluene. The toluene washing liquids were added to the organic layer previously separated, and the resulting organic layer was washed with a saturated sodium hydrogen carbonate aqueous solution and a sodium chloride aqueous solution, successively. The solvent was removed from the toluene solution to obtain 28.7 g of a viscous oily substance. The substance was subjected to distillation under reduced pressure to isolate 25.6 g (90% yield) of the aimed-at Compound (I).

EFFECTS OF THE INVENTION

According to the present invention, Compound (I) can be obtained conveniently in high yield.

What is claimed is:

1. A process for producing 3,9-bis(2-chloroethyl)-2,4,8,10-tetraoxaspiro[5.5]undecane comprising a step of reacting acrolein, pentaerythritol, and hydrogen chloride at one step.

2. The process according to claim 1, wherein hydrochloric acid is used as said hydrogen chloride.

* * * * *